US005914346A

United States Patent [19]
Cook et al.

[11] Patent Number: 5,914,346
[45] Date of Patent: Jun. 22, 1999

[54] METHODS OF TREATING ANIMALS TO ENHANCE NATURAL KILLER LYMPHOCYTE FUNCTION

[75] Inventors: Mark E. Cook, Madison, Wis.; Sohee Kim, Pusan, Rep. of Korea; Michael W. Pariza; Danielle DeVoney, both of Madison, Wis.

[73] Assignee: Wisconsin Alumni Research Foundation, Madison, Wis.

[21] Appl. No.: 08/963,740

[22] Filed: Nov. 4, 1997

Related U.S. Application Data

[60] Provisional application No. 60/030,394, Nov. 5, 1996.
[51] Int. Cl.$^6$ .......................... A61K 38/00; A61K 31/20; A61K 31/70
[52] U.S. Cl. .................................. 514/558; 514/2; 514/27
[58] Field of Search ................................... 514/27, 558, 2

[56] References Cited

U.S. PATENT DOCUMENTS

| | | | |
|---|---|---|---|
| 4,282,265 | 8/1981 | Theuer | 426/607 |
| 4,603,142 | 7/1986 | Burger et al. | 514/456 |
| 4,868,001 | 9/1989 | Maruta | 426/623 |
| 4,888,326 | 12/1989 | Horrobin | 514/27 |
| 5,017,614 | 5/1991 | Cook et al. | 514/558 |
| 5,045,338 | 9/1991 | Klemann et al. | 426/611 |
| 5,068,119 | 11/1991 | Klemann et al. | 426/601 |
| 5,070,104 | 12/1991 | Pariza et al. | 514/549 |
| 5,428,072 | 6/1995 | Cook et al. | 514/560 |
| 5,430,066 | 7/1995 | Cook et al. | 514/558 |
| 5,470,839 | 11/1995 | Laughlin et al. | 514/53 |
| 5,554,646 | 9/1996 | Cook et al. | 514/560 |
| 5,760,082 | 6/1998 | Cook et al. | 514/560 |
| 5,814,663 | 9/1998 | Cook et al. | 514/560 |

FOREIGN PATENT DOCUMENTS

| | | |
|---|---|---|
| 0579901 A1 | 3/1993 | European Pat. Off. . |
| 0779033 A1 | 6/1997 | European Pat. Off. . |
| 61-216658 | 9/1986 | Japan . |
| 6-276939 | 10/1994 | Japan . |
| WO90/09110 | 8/1990 | WIPO . |
| WO92/10105 | 6/1992 | WIPO . |
| WO 94/16690 | 8/1994 | WIPO . |

OTHER PUBLICATIONS

Miller, et al., "Feeding Conjugated Linoleic Acid to Animals Partially Overcomes Catabolic Responses Due to Endotoxin Injection", *Biochemical and Biophysical Research Communications*, 198 (3): 1107–1112 (1994).

Ha et al., "Anticarcinogens from Fried Ground Beef: Heat–Altered Derivatives of Linoleic Acid", *Carcinogenesis* 8(12):1881–1887 (1987).

Ha et al., "Newly Recognized Anticarcinogenic Fatty Acids: Identification and Quantification in Natural and Processed Cheeses", *J. Agric. Food Chem.* 37:75–81 (1989).

Pariza, M. W., "What's New (and Old) About CLA", *Food Research Institute 1988 Annual Fall Meeting* (Oct. 1988).

Pariza et al., "Chemoprevention by CLA: A Role for Prostaglandins", *Proc. Annu. Meet. Am. Assoc. Cancer Res.* vol. 34 (1993).

Pariza et al., "Conjugated Linoleic Acid (CLA) Reduces Body Fat" (Abstract), *FASEB Journal* 10(3) (Mar. 6, 1996).

*The Merck Index: An Encyclopedia of Chemicals, Drugs and Biologicals–Tenth Edition,* edited by Marth Windholz et al., Merck & Co., Inc. N.J. (1983).

*The Merck Veterinary Manual: A Handbook of Diagnosis and Therapy for the Veterinarian–Fifth Edition,* edited by Otto Siegmund et al., Merck & Co., Inc. N.J. (1979).

Wong et al., "Effects of Dietary Conjugated Linoleic Acid on Lyphocyte Function and Growth of Mammary Tumors in Mice", *Anticancer Res.* 17(2a):987–993 (1997).

Belury, M.A. and Anna Kempa–Steczko, "Conjugated Linoleic Acid Modulates Hepatic Lipid Composition in Mice", *Lipids* 32(2) 199–203 (1997).

Chin et al., "Conjugated Linoleic Acid (9, 11–and 10, 12–Octadecadienoic Acid) is Produced in Conventional But Not Germ–Free Rats Fed Linoleic Acid", *Nutrient Metabolism,* American Institute of Nutrition 694–701 (1994).

Chin et al., "Conjugated Linoleic Acid is a Growth Factor for Rats as Shown by Enhanced Weight Gain and Improved Feed Efficiency", *Biochemical and Molecular Roles of Nutrients,* American Institute of Nutrition 2344–2349 (1994).

Chin et al., "Dietary Sources of Conjuated Dienoic Isomers of Linoleic Acid, a Newly Recognized Class of Anticarcinogens", *J. Food Composition Analysis* 5:185–197 (1992).

Fogerty et al., "Octadeca–9,11–Dienoic Acid in Foodstuffs and in the Lipids of Human Blood and Breast Milk", *Nutrition Reports International* 38(5): 937–944 (1988).

Gurr, Mike, "A trans Fatty Acid that is Good To Eat? Conjugated Linoleic Acid", *Lipid Technology* 133–135 (1995).

Ha et al., "Inhibition of Benzo(α)Pyrene–Induced Mouse Forestomach Neoplasia by Conjugated Dienoic Derivatives of Linoleic Acid", *Cancer Research* 50:1097–1101 (1990).

Ip et al., "Mammary Cancer Prevention by Conjugated Dienoic Derivative of Linoleic Acid", *Cancer Research* 51:6118–6124 (1991).

Kammerlehner, J., "Linolsäure und Konjugierte Linolsäuren–ihr Vorkommen im Milchfett, ihre Biologische Bedeuung–" *Milchinhaltsstoffe* 1268–1272 (1995).

Lin et al., "Survey of the Conjugated Linoleic Acid Contents of Dairy Products", *J. Dairy Sci.* 78:2358–2365 (1995).

(List continued on next page.)

*Primary Examiner*—Theodore J. Criares
*Attorney, Agent, or Firm*—Quarles & Brady LLP

[57] ABSTRACT

A method of enhancing the activity of natural killer lymphocytes and a method for increasing the basal level of natural killer activity in an animal include the step of administering orally or parenterally to said animal a safe amount of CLA, said amount being effective to enhance the activity of killer lymphocytes or to enhance the basal activity of killer lymphocytes in the animal.

12 Claims, 5 Drawing Sheets

OTHER PUBLICATIONS

McGuire et al., "Conjugated Linoleic Acid Concentration of Human Milk and Infant Formulae", *Human Milk and Lactation* 1:3186–3189 (1996).

Miller et al., "Feeding Conjugated Linoleic Acid to Animals Patrially Overcomes Catabolic Responses Due to Endotoxin Injection", *Biochem. and Biophy. Research Communications* 198(3):1107–1112 (1994).

Pariza, M. W., "Conjugated Linoleic Acid, a Newly Recognised Nutrient", *Chemistry and Industry* 464–466 (Jun. 19, 1997).

Pariza, M.W., "CLA, A New Cancer Inhibitor in Dairy Products", *Bulletin of the IDF* 257:29–30 (1991).

Pariza, M.W., "Designer Foods: Effects on Development of Cancer", *J. National Cancer Institute Monographs* 12:105–107 (1992).

Pariza, M.W., "CLA and HEMF: Newly Recognized Anticarcinogenic Antioxidants", in *Active Oxygen, Lipid Peroxides, and Antioxidants,* Yagi, K. editor pp. 359–365, Japan Sci. Soc. Press, Tokyo (1993).

Council on Scientific Affairs, American Medical Association, "Report of the Council on Scientific Affairs: Diet and Cancer: Where Do Matters Stand?", *Arch. Intern Med.,* 153:50–56 (1993).

Sarkar, Gobinda, "Beneficial Ghee?", *Nature* 352(22):673 (1991).

Shanta, N.C. and E.A. Decker," Conjugated Linoleic Acid Concentrations in Processed Cheese Containing Hydrogen Donors, Iron and Dairy–Based Additives", *Food Chemistry* 47:257–261 (1993).

Shantha et al., "Conjugated Linoleic Acid Concentrations in Dairy Products as Affected by Processing and Storage", *J. Food Science* 60(4): 695–697,720 (1995).

122:131629x, 6001 Chemical Abstracts, 122(11): 972 (1995).

Sieber, R., "Konjugierte Linolsäuren in Lebensmitteln:eine Übersicht: Conjugated Linoleic Acids in Foods: A Review", *Nutrition/Ernährung* 19(6):265–270 (1995).

[5,914,346]

METHODS OF TREATING ANIMALS TO ENHANCE NATURAL KILLER LYMPHOCYTE FUNCTION

CROSS-REFERENCE TO RELATED APPLICATIONS

This application claims the benefit under 35 U.S.C. §119 (e) of provisional patent application Ser. No. 60/030,394, filed Nov. 5, 1996.

STATEMENT REGARDING FEDERALLY SPONSORED RESEARCH OR DEVELOPMENT

Not applicable.

BACKGROUND OF THE INVENTION

The present application generally relates to methods of treating animals, including humans. More particularly, it relates to methods of treating animals to enhance the activity of natural killer lymphocytes.

It is known that the natural killer lymphocytes in animals, including humans, are capable of disabling or destroying cells which have acquired foreign characteristics, such as tumor cells or virus-infected cells. Enhancing the activity of killer lymphocytes also could be effective in preventing the formation of tumor cells and virus-infected cells and enhancing the immune defenses of an animal against mutated cells of the animal or pathogen infected cells.

Obviously, it would be advantageous to have a method for enhancing the activity of natural killer lymphocytes in animals.

BRIEF SUMMARY OF THE INVENTION

It is the object of the present invention to disclose a method of enhancing the activity of natural killer lymphocytes in animals.

It is another object of the present invention to disclose a method for increasing the basal level of natural killer activity in an animal.

We have discovered a method of enhancing the activity of killer lymphocytes in an animal, including a human, which comprises administering to the animal a safe and effective amount of a conjugated linoleic acid, such as 9,11-octadecadienoic acid and 10,12-octadecadienoic acid, or active derivatives thereof, such as non-toxic salts, active esters, such as triglycerides, and mixtures thereof.

The conjugated linoleic acids, their non-toxic salts, active esters, active isomers, active metabolics, and mixtures thereof are referred to herein as "CLA."

It will be apparent to those skilled in the art that the forementioned objects and other advantages may be achieved by the practice of the present invention.

DETAILED DESCRIPTION OF THE INVENTION

Figure 1:
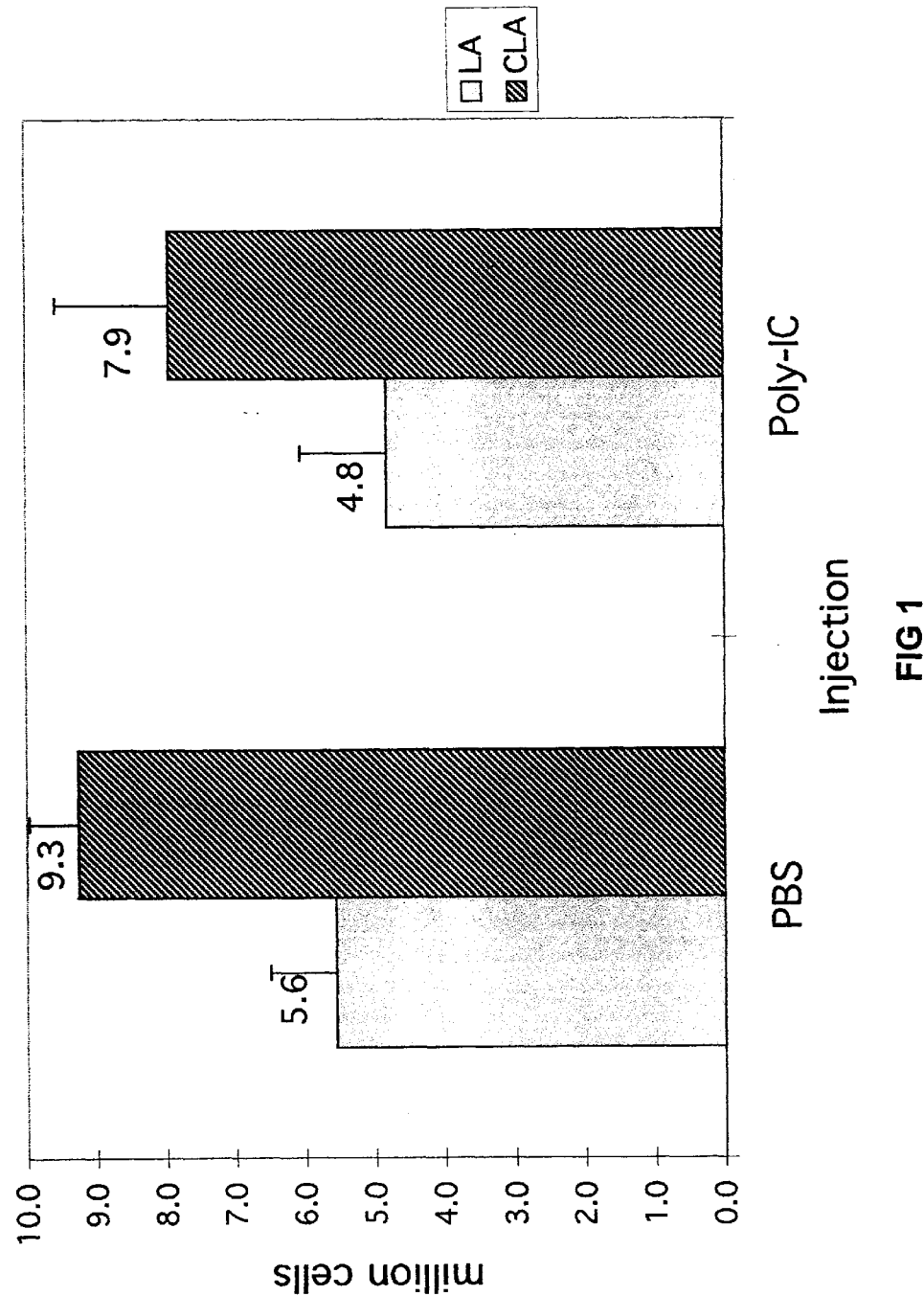
FIG. 1 reports the average number of splenic lymphocytes harvested from the spleens of animals fed either CLA or LA and which additionally were either unstimulated or stimulated with poly-IC to enhance NK activity.

In the preferred method of the present invention for enhancing the activity of killer lymphocytes in an animal, a safe and effective amount of CLA is administered to the animal.

Since CLA is a natural food ingredient and it is relatively non-toxic, the amount of CLA which can be administered is not critical as long as it is enough to be effective.

The methods of the present invention may take several embodiments. In one embodiment, the CLA is administered to an animal in a pharmaceutical or veterinary composition containing a safe and effective dose of the CLA. In another embodiment, the animal is fed a food that has been enriched with CLA.

The animal feeds and pharmaceutical preparations for use in the methods of the present invention are those containing the CLA in combination with a conventional animal feed (e.g. poultry feed), human food supplement, or approved pharmaceutical diluent.

Active forms of CLA include the free conjugated linoleic acids, the active isomers of those acids, non-toxic salts thereof, active esters of those acids, such as the triglycerides, methyl and ethyl esters, and other active chemical derivatives thereof, and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)).

The free acid forms of the CLA may be prepared by isomerizing linoleic acid. The non-toxic salts of the free CLA acids may be made by reacting the free acids with a non-toxic base. Natural CLA may also be prepared from linoleic acid by the action of W $^{12}$-cis, W $^{11}$-transisomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The free acids are readily converted into a non-toxic salt, such as the sodium, potassium or calcium salts, by reacting chemically equivalent amounts of the free acid with an alkali hydroxide at a PH of about 8 to 9.

Theoretically, 8 possible geometric isomers of 9,11- and 10,12-octadecadienoic acid (c9,c11; c9,t11; t9,c11; t9,t11;

c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11and 10,12-, t9,c11- and c11,t12-octadecadienoic acids). The 11,13-isomer might be produced as a minor product from c9,c12-octadecadienoic acid or from its isomeric forms during processing.

The CLA, in addition to being added to an animal's food, can be administered in the form of pharmaceutical or veterinary compositions, such as tablets, capsules, solutions or emulsions to the animal or the humans. The exact amount to be administered, of course, depends upon the form of CLA employed and the route of administration, and the nature of the animal's or human's condition. Generally, the amount of CLA employed as a pharmaceutical will range from about 100 mgm to about 20,000 mg of CLA (calculated as the free acids) per day. However, the upper limit of the amount to be employed is not critical because CLA is relatively non-toxic. The amounts of CLA (calculated as the free acids) to be added to food as an additive can range from 0.01% to 2.0% or more by weight of the food.

The practice of the present invention is further illustrated by the following experiments which were conducted.

The object of the first experiment was to determine if CLA prevented cancerous growth by enhancing immune cell activity (natural killer cells) responsible for destroying tumor cells.

In the first experiment, twenty-four mice were fed zero or 0.5% CLA for 4 weeks. Prior to sacrificing the mice, half of the mice on each dietary treatment were injected with 1 mg/kg body weight of endotoxin or phosphate-buffered saline (PBS). Spleens were harvested from these mice, and lymphocytes were isolated. These lymphocytes were co-cultured with a tumor cell line to assess cytotoxic activity of the natural killer cells in spleen. In mice fed CLA, which had been injected with PBS or endotoxin, there were significant enhancements of natural killer lymphocyte activity. In addition, lymphocytes isolated from normal mice and cultured with CLA also displayed enhanced killer activity against the tumor cell line.

TABLE 1

Natural killer cell cytotoxicity
mice fed 4 weeks
Target $5 \times 10^4$
Effector Target x 60,20
3 days cul.

|  | Control (PBS) | Control (LPS) | CLA (PBS) | CLA (LPS) |
|---|---|---|---|---|
| Target X 60 | | | | |
|  | 19 | 32.1 | 24 | 37.9 |
|  | 27.2 | 55.2 | 50.8 | 67.3 |
|  | 30 | 45.7 | 48.1 | 58.3 |
|  | 31.5 | 51.3 | 37.3 | 66.4 |
|  | 19.3 | 54.5 | 32.9 | 52.9 |
|  | 20.6 | 44 | 30.6 | 50.9 |
| mean | 24.6 | 47.13333 | 37.28333 | 55.61667 |
| SD | 5.147491 | 7.901195 | 9.487082 | 10.02903 |
| SE | 2.101455 | 3.22565 | 3.873085 | 4.094333 |
| Target X 20 | | | | |
|  | 10.3 | 22 | 25 | 23.6 |
|  | 11.4 | 25 | 15.2 | 25.6 |
|  | 18.4 | 21.1 | 16.8 | 18.4 |
|  | 16.5 | 17.1 | 16 | 16.3 |
|  | 11.1 | 22.6 | 17.7 | 27.3 |
|  | 17.8 | 25.5 | 26.5 | 26.1 |
| mean | 14.25 | 22.21667 | 19.53333 | 22.88333 |
| SD | 3.379719 | 2.773335 | 4.481691 | 4.106668 |
| SE | 1.379764 | 1.132209 | 1.829643 | 1.67654 |
| Spleen Weight/Body weight | | | | |
|  | 0.003 | 0.0054 | 0.0035 | 0.0045 |
|  | 0.0017 | 0.0049 | 0.0038 | 0.0061 |
|  | 0.0025 | 0.0071 | 0.0039 | 0.0064 |
|  | 0.0025 | 0.0038 | 0.0044 | 0.0058 |
|  | 0.0028 | 0.0045 | 0.0036 | 0.0065 |
|  | 0.0024 | 0.0048 | 0.0029 | 0.0057 |
|  | 0.0034 | 0.0042 | 0.0029 | 0.0041 |
|  | 0.0025 | 0.0073 | 0.003 | 0.0052 |
| Mean | 0.0026 | 0.00525 | 0.0035 | 0.005538 |
| SD | 0.000164 | 0.000428 | 0.000179 | 0.000289 |
| SE | 0.000464 | 0.001211 | 0.000505 | 0.000817 |

The second experiment confirmed the observation of the first experiment that NK cell activity increased in animals fed a diet that comprises CLA. At the same time, the second experiment also demonstrated (1) that basal per-cell NK activity is higher in a CLA-fed animal than in an LA-fed animal, (2) that the spleen is larger and the number of spleen cells is higher in a CLA-fed animal than in an LA-fed animal, and (3) that the proportion of NK cells among splenic lymphocytes is maintained after consuming CLA.

Three week old weanling C57BL/6 male mice were housed, four to a cage, under standard conditions. The mice were fed a powdered diet supplemented with either 0.5% linoleic acid (LA) or 0.5% conjugated linoleic acid (CLA) for twenty-eight days. Thirty-six hours before animal sacrifice, one-half of the animals receiving each dietary treatment were injected peritoneally with one hundred microliters of dilute polyinosinic-polycytidylic acid (poly-IC), an agent known to stimulate natural killer (NK) cell activity in vivo. Splenic lymphocytes were isolated from spleen homogenates by gradient centrifugation. The splenic lymphocytes were counted and three serial dilutions were prepared. Spleen samples were not pooled.

The average number of lymphocyte cells harvested per spleen (FIG. 1) was significantly higher in CLA-fed mice than in LA-fed mice. The number of lymphocyte cells per spleen appeared to be largely independent of whether the mice were stimulated to increase NK activity.

Figure 2:
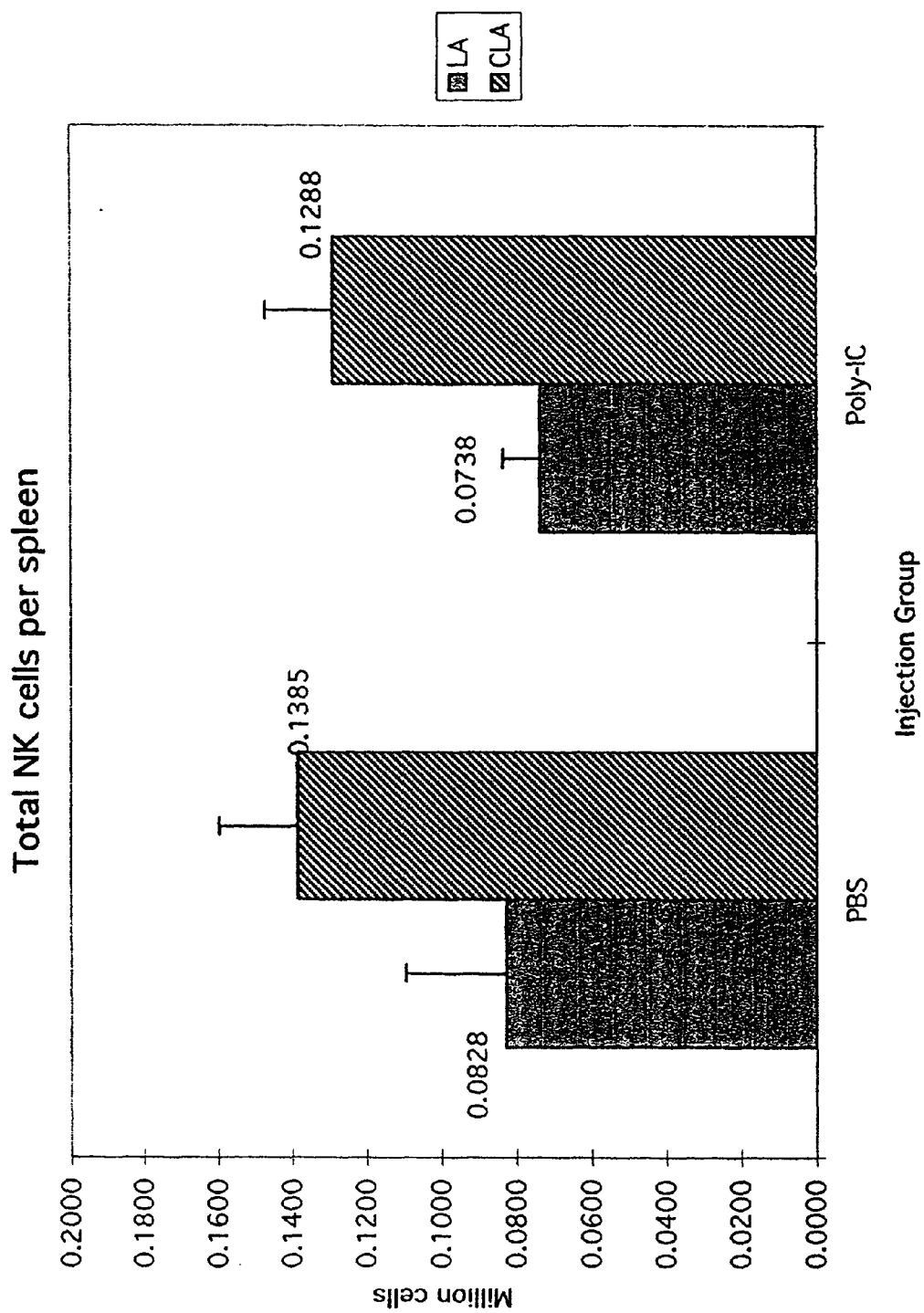
FIG. 2 reports the average number of NK cells per spleen harvested from animals fed either CLA or LA and which additionally were either unstimulated or stimulated with poly-IC to enhance NK activity.

The average number of NK cells per spleen (FIG. 2) was also significantly higher in CLA-fed mice than in LA-fed mice. Again, the number of NK cells isolated per spleen appeared to be largely independent of whether the mice were stimulated to increase NK activity.

Figure 3:
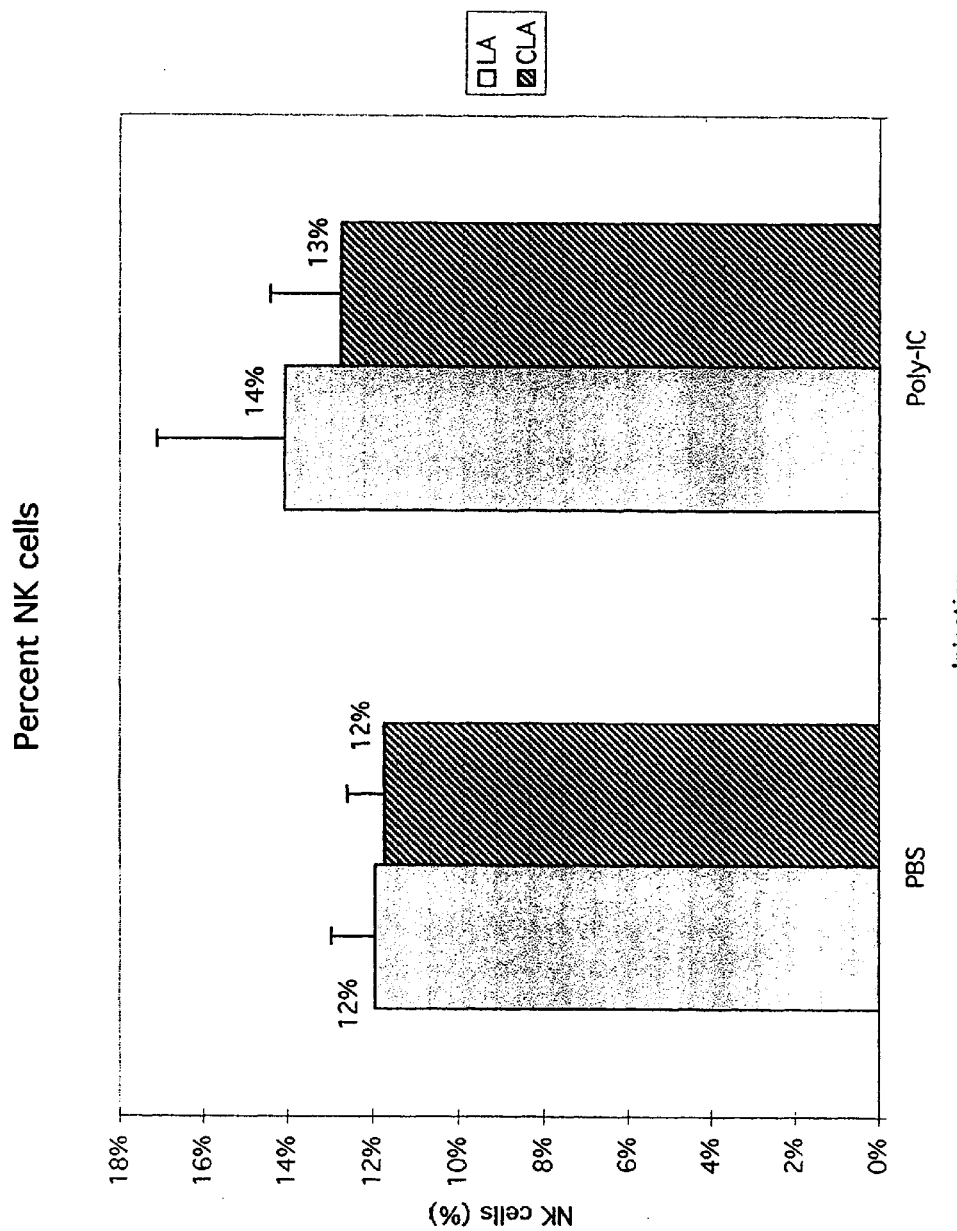
FIG. 3 reports the percent of NK cells in splenic lymphocytes harvested from animals fed either CLA or LA and which additionally were either unstimulated or stimulated with poly-IC to enhance NK activity.

The percent of NK cells among splenic lymphocytes (FIG. 3) was fairly constant and appeared to be unaffected either by stimulation with poly-IC or by the presence of CLA or LA in the diet.

NK activity in the isolated spleen cells was assessed in a standard NK assay run in triplicate for each animal using the YAC-1 lymphoma cell line as a target. YAC-1 cells (commercially available from the American Type Culture Collection, Rockville, Md. (Accession Number TIB-160)) were co-cultured for four hours in 96-well plates with splenic lymphocytes at 3 effector-to-target (E:T) cell ratios in the range of 5 to 35. To quantify the cells that remained alive at the end of the four hour assay, the tetrazolium dye MTT was added and after four more hours of incubation a formamide-based stopping solution was added. The plates were incubated overnight for color development. Absorbance at 562 nanometers was measured for each well. Associated blanks and controls were run on each plate.

From the absorbance data, a regression curve was created to relate NK activity to E:T ratio. The average expected NK activity at the E:T ratio of 11.0 was determined for each diet/injection group and standard deviations and standard errors were calculated.

Figure 4:
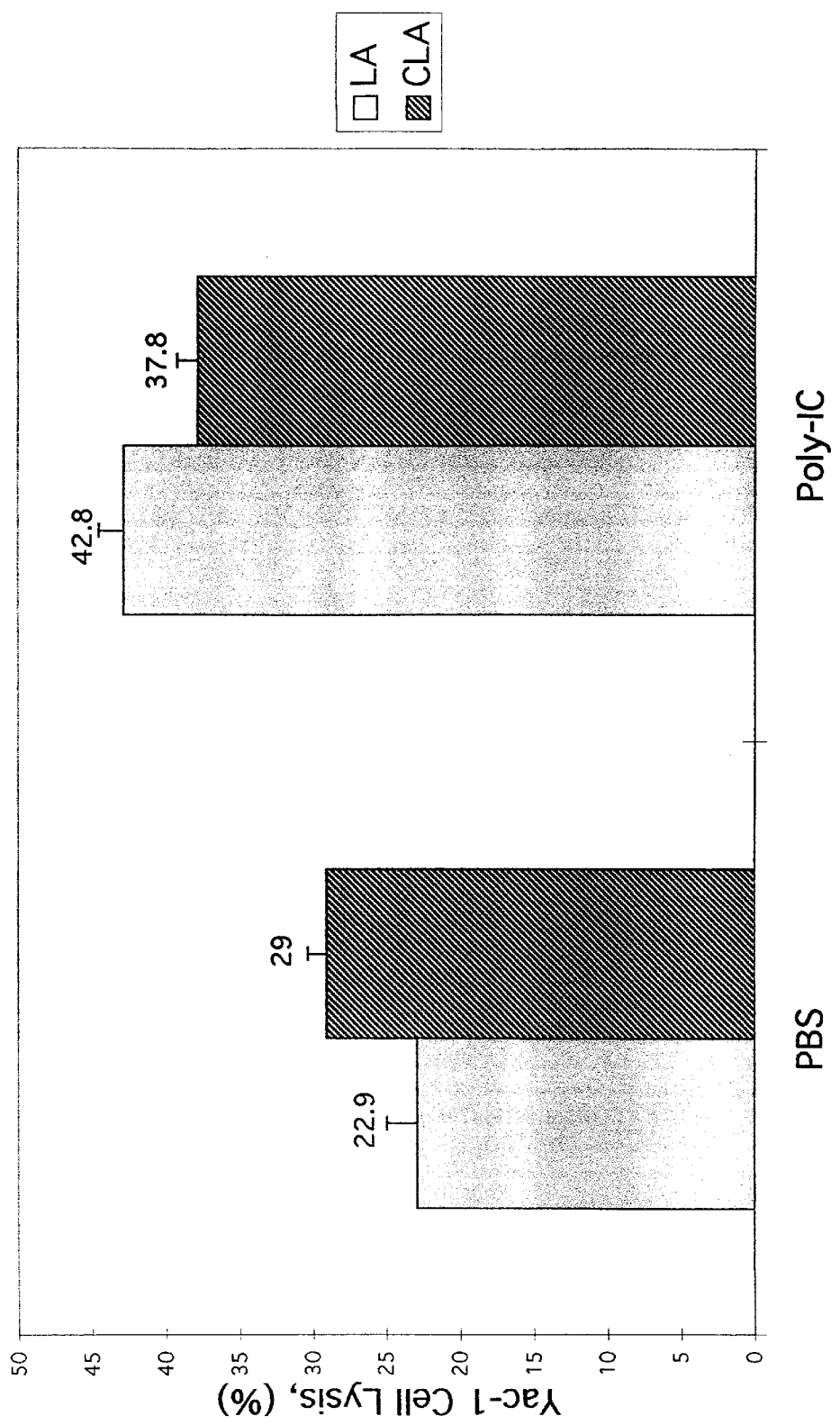
FIG. 4 reports the NK activity of splenic lymphocytes harvested from animals fed either CLA or LA and which additionally were either unstimulated or stimulated with poly-IC to enhance NK activity.

FIG. 4 presents NK activity data normalized to reflect the same number of cells in each well. The left side of FIG. 4 depicts results for animals that were not stimulated with poly-IC, while the right side reports results for poly-IC stimulated animals. Unstimulated animals (FIG. 4, left) fed a diet supplemented with 0.5% CLA exhibit increased NK activity in splenic lymphocytes relative to animals fed a comparable amount of LA.

Figure 5:
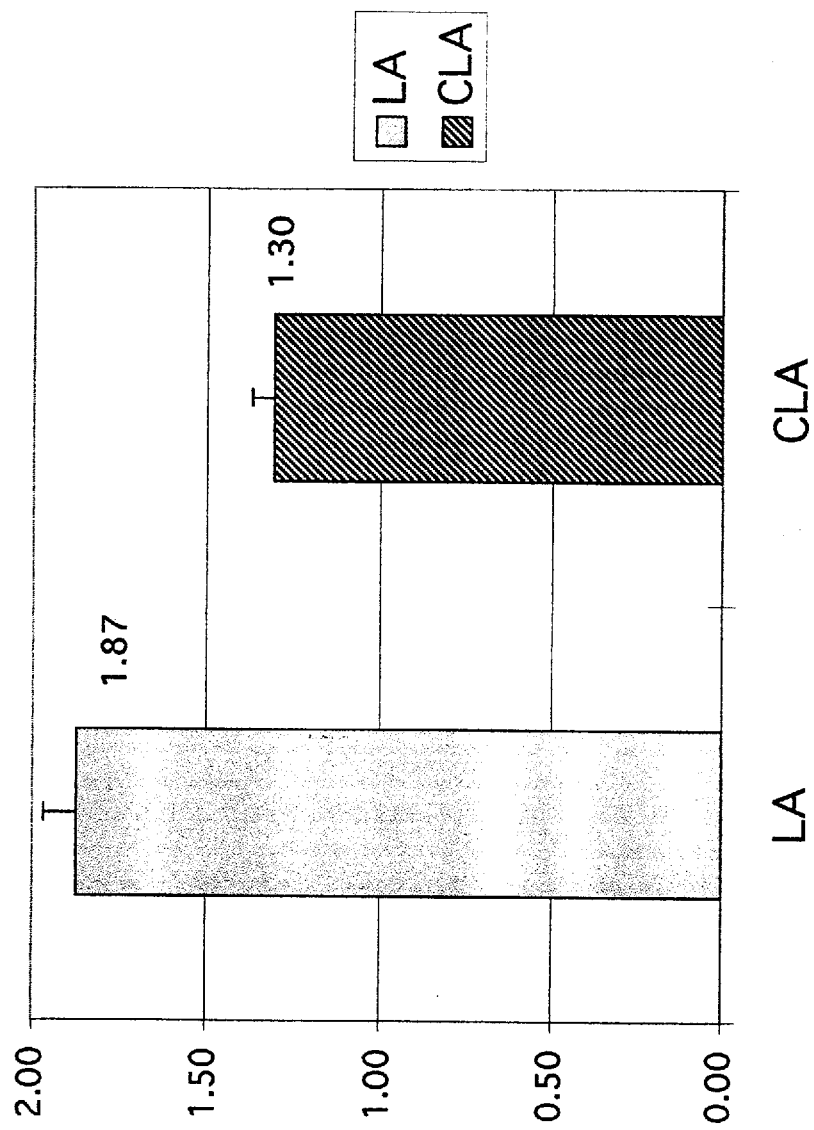
FIG. 5 reports the difference in fold-increase in NK activity after stimulation with poly-IC between animals fed CLA or LA.

Poly-IC-stimulated mice (FIG. 4, right) fed with LA appear to have a higher level of NK activity than splenic lymphocytes from CLA-fed mice. However, when the basal level of NK activity (in the PBS injected mice) is compared against the stimulated activity in poly-IC stimulated mice, for each diet, LA fed mice have a 1.87 fold increase in NK activity whereas CLA fed mice have a 1.30 fold increase (FIG. 5).

Without further analysis, these data could mislead one to believe that LA has a greater effect than CLA. However, a more proper analysis is that mice fed with CLA have a higher basal level of NK activity than mice fed with LA and achieve a high level of NK activity in stimulated mice with a lower overall increase in activity. It is the higher basal level of NK activity in CLA-fed mice that is of particular interest because it maintains the surveillance function of NK cells without overstimulating the immune system.

This increased basal level activity comes about not only by virtue of increased activity per cell, but also from the observation made here that CLA ingestion increases both the size of the spleen and the number of cells it contains. Thus, an animal fed with CLA is better equipped to deal with immune challenges than an animal that has not been fed CLA and which has a lower basal level of natural killer cell activity.

A third important component of this aspect of the invention is that a proportionally constant level of NK cell found in animals fed CLA or not fed CLA. It would not have been predictable that the NK cells would be maintained, as it is known that various treatments can affect subpopulations of immune system cells. It would be, for example, unacceptable for the cells to have an acceptably high activity, but for the cells to be present in such low number as to be immunologically irrelevant. This can have important therapeutic ramifications in that it is clear that, after consuming CLA, animals maintain a number of cells in the NK subpopulation that is sufficiently high to permit immune surveillance without placing the immune system of the animal into an overstimulated (hyperactive) state. Since control-fed mice undergo a much greater proliferative response than CLA-fed mice upon immune challenge (endo or poly IC), the relative requirement for hyperimmunity is likely to have adverse effects on other physiological function in non-CLA-fed mice. CLA-fed animals naturally have higher numbers of NK cells, hence those animals do not have to go through a hyperactive immune process to reach cell numbers sufficient for immune defense. Moreover, it is shown herein that the NK cells themselves have high NK activity on a per-cell basis.

In summary, then, the applicants have herein shown that a method for enhancing a basal level of natural killer cell activity in an animal, includes the step of administering a safe amount of CLA to the animal, the amount being effective to increase the basal level of NK activity over the level observed in animals not fed CLA.

It will be readily apparent to those skilled in the art that a number of modifications or changes may be made without departing from the spirit and scope of the present invention.

We claim:

1. A method of maintaining or enhancing the activity of killer lymphocytes in an animal, said method comprising administering orally or parenterally to said animal a safe amount of CLA, said amount being effective to enhance the activity of killer lymphocytes.

2. The method as claimed in claim 1 wherein the CLA is administered orally to the animal in a food.

3. The method as claimed in claim 1 wherein the CLA is administered as a non-toxic salt of CLA, as an active ester of CLA or as a mixture thereof.

4. A method of increasing basal activity of killer lymphocytes in an animal, said method comprising administering orally or parenterally to said animal a safe amount of CLA, said amount being effective to enhance the basal activity of killer lymphocytes in the animal.

5. The method as claimed in claim 4 wherein the CLA is administered orally to the animal in a food.

6. The method as claimed in claim 4 wherein the CLA is administered as a non-toxic salt of CLA, as an active ester of CLA or as a mixture thereof.

7. A method of preventing a hyperactive killer cell response following immune challenge, said method comprising administering orally or parenterally to said animal a safe amount of CLA, said amount being effective to enhance the basal activity of killer lymphocytes in the animal.

8. The method as claimed in claim 7 wherein the CLA is administered orally to the animal in a food.

9. The method as claimed in claim 7 wherein the CLA is administered as a non-toxic salt of CLA, as an active ester of CLA or as a mixture thereof.

10. A method of maintaining or enhancing anti-tumor cell activity of killer lymphocytes in an animal, said method comprising administering orally or parenterally to said animal a safe amount of CLA, said amount being effective to enhance the activity of killer lymphocytes.

11. The method as claimed in claim 10 wherein the CLA is administered orally to the animal in a food.

12. The method as claimed in claim 10 wherein the CLA is administered as a non-toxic salt of CLA, as an active ester of CLA or as a mixture thereof.

* * * * *